United States Patent [19]

Katsumata et al.

[11] Patent Number: 5,407,824

[45] Date of Patent: Apr. 18, 1995

[54] RECOMBINANT CORYNEFORM BACTERIUM FOR PRODUCING L-TRYPTOPHAN

[75] Inventors: Ryoichi Katsumata, Tokyo; Masato Ikeda, Sagamihara; Keiko Nakanishi, Tokyo, all of Japan

[73] Assignee: Kyowa Hakko Kogyo Co., Ltd., Tokyo, Japan

[21] Appl. No.: 531,441

[22] Filed: May 30, 1990

[30] Foreign Application Priority Data

Jun. 6, 1989 [JP] Japan ................................ 1-143693

[51] Int. Cl.$^6$ .................. C12N 1/21; C12N 15/77
[52] U.S. Cl. ...................... 435/252.32; 435/108; 435/183; 435/172.3; 435/320.1; 536/23.1; 536/23.2; 536/23.7
[58] Field of Search ............. 435/69.1, 71.2, 91, 435/172.1, 172.3, 183, 108, 320.1, 252.32, 843, 840; 536/23.1, 23.2, 23.7; 935/6, 9, 10, 22, 27, 29, 33, 38, 39, 59, 60, 61, 66, 72

[56] References Cited

U.S. PATENT DOCUMENTS

| | | | |
|---|---|---|---|
| 4,371,614 | 2/1983 | Andeson et al. | 435/108 |
| 4,489,160 | 12/1984 | Katsumata et al. | 435/91.4 |
| 4,500,640 | 2/1985 | Katsumata et al. | 435/252.32 |
| 4,617,267 | 10/1986 | Katsumata et al. | 435/91.4 |
| 4,710,471 | 12/1987 | Katsumata et al. | 435/253.32 |
| 5,034,318 | 7/1991 | Miwa et al. | 435/108 |

FOREIGN PATENT DOCUMENTS

| | | |
|---|---|---|
| 0124048 | 11/1984 | European Pat. Off. . |
| 136359 | 4/1985 | European Pat. Off. . |
| 183175 | 6/1986 | European Pat. Off. . |
| 149082 | 7/1986 | Japan . |
| 62-79775 | 4/1987 | Japan . |
| 64-67178 | 3/1989 | Japan . |
| 64-67179 | 3/1989 | Japan . |
| 8701130 | 2/1987 | WIPO . |

OTHER PUBLICATIONS

Ikeda, et al., *Improved Tryptophan (trp) Producing Microorganism Corynebacterium glutamicum*, J. Japan Agr. Chem. Assoc., 63(3) p. 701 (1989).

Patent Abstracts of Japan, vol. 13, No. 273 (C-609) [3621], Jun. 22, 1989.

Patent Abstracts of Japan, vol. 10, No. 345 (C-386) [2401], Nov. 20, 1986.

K. L. Tobey and G. A. Grant, The Journal of Biological Chemistry, vol. 261, No. 26, pp. 12179–12183 (Sep. 15, 1986).

Matsui et al., 1988, Agric. Biol. Chem., 52(7): 1863–1865.

Somerville, 1983, In: Amino Acids; Biosynthesis and Regulation, Addison-Wesley, Helmann et al. (eds), pp. 351–361.

Stauffer, 1983, In: Amino Acids: Biosynthesis and Regulation, Addison-Wesley, Hermann et al. (eds), pp. 103–113.

Primary Examiner—Richard A. Schwartz
Assistant Examiner—J. LeGuyader
Attorney, Agent, or Firm—Fitzpatrick, Cella, Harper & Scinto

[57] ABSTRACT

L-tryptophan is produced by constructing a recombinant DNA composed of a vector DNA and DNA fragments bearing all of genetic information relating to the synthesis of DS, AS, PRT, PRAI, InGPS, TS and PGDH, introducing the recombinant DNA into a microorganism belonging to the genus Corynebacterium or Brevibacterium, culturing the microorganism in a medium, and recovering L-tryptophan accumulated in the culture.

2 Claims, 2 Drawing Sheets

RECOMBINANT CORYNEFORM BACTERIUM FOR PRODUCING L-TRYPTOPHAN

FIELD OF THE INVENTION

The present invention relates to a process for producing L-tryptophan which comprises culturing in a medium a microorganism belonging to the genus Corynebacterium or Brevibacterium and carrying a recombinant DNA composed of a vector DNA and DNA fragments bearing all the genes relating to the synthesis of 3-deoxy-D-arabino-heptulosonate-7-phosphate synthase (hereinafter referred to as "DS"), anthranilate synthase (hereinafter referred to as "AS"), anthranilate phosphoribosyl transferase (hereinafter referred to as "PRT"), N-5'-phosphoribosyl anthranilate isomerase (hereinafter referred to as "PRAI"), indole-3-glycerol phosphate synthase (hereinafter referred to as "InGPS"), tryptophan synthase (hereinafter referred to as "TS") and 3-phosphoglycerate dehydrogenase (hereinafter referred to as "PGDH"); allowing L-tryptophan to accumulate in the culture; and recovering L-tryptophan therefrom. The present invention, therefore, concerns with the industrial field of biology, particularly with the manufacture of L-tryptophan which is useful in the pharmaceutical and animal feed industries.

PRIOR ART

By recombinant DNA technology, various strains belonging to the genus Corynebacterium or Brevibacterium and capable of producing L-tryptophan have been constructed. For example, a recombinant DNA containing an AS gene [Japanese Published Unexamined Patent Application No. 156292/1984 (EP 136359-A)], a recombinant DNA containing a PRT gene, a PRAI gene, an InGPS gene and a TS gene (Japanese Published Unexamined Patent Application No. 149082/1986), a recombinant DNA containing a DS gene [Japanese Published Unexamined Patent Application No. 51980/1987 (EP 183175-A)], a recombinant DNA containing PRAI-InGPS genes (Japanese Published Unexamined Patent Application No. 79775/1987), and a recombinant DNA containing a DS gene and AS-TS genes [journal of Japan Agricultural Chemistry Association, 63, (3), p.701 (1989)] have hitherto been known.

Further processes for producing L-tryptophan by using L-tryptophan-producing microorganism belonging to the genus Bacillus and incorporating therein a recombinant DNA containing genes relating to the biosynthesis of serine (Japanese Published Unexamined Patent Application Nos. 67178/1989 and 67179/1989) have been also known to the art.

Problems to be solved by the Invention and Means for solving the Problem

In recent years, a need for L-tryptophan has increasingly grown so much that an improved process for producing this amino acid is needed. The inventors, in search of constructing an excellent L-tryptophan-producing microorganism by using recombinant DNA technology, have surprisingly found that the introduction of a recombinant DNA containing DNA fragments bearing all of genetic information relating to the synthesis of DS, AS, PRT, PRAI, InGPS, TS and PGDH into a strain of the genus Corynebacterium or Brevibacterium increases L-tryptophan productivity of the strains. The collective use of all of the genes of DS, AS, PRT, PRAI, InGPS, TS and PGDH has never been known to the art. The fact that the simultaneous amplification of all of these genes allows considerable increase in L-tryptophan production has been established for the first time by the present invention.

EFFECT OF THE INVENTION

According to the present invention, it is possible to enhance L-tryptophan productivity of a strain of the genus Corynebacterium or Brevibacterium by introducing a recombinant DNA bearing all of genetic information relating to the synthesis of DS, AS, PRT, PRAI, InGPS, TS and PGDH of microbial origin into the strain.

The present invention will further be described in detail hereinafter.

The present invention provides a process for producing L-tryptophan which comprises culturing in a culture medium a microorganism belonging to the genus Corynebacterium or Brevibacterium and carrying a recombinant DNA composed of a vector and DNA fragments bearing all of genetic information relating to the synthesis of DS, AS, PRT, PRAI, InGPS, TS and PGDH, allowing L-tryptophan to accumulate in the culture, and recovering L-tryptophan therefrom.

As the DNA fragments mentioned above, those derived from microorganisms belonging to the genus Corynebacterium or Brevibacterium may be used.

As the donor strains of the individual genes, any microorganisms which are prototrophic in the biosynthesis of aromatic amino acids may be used. Particularly preferred genes are those derived from procaryotes such as bacteria belonging to the genus Escherichia, Corynebacterium or Brevibacterium, and those derived from aromatic amino acid-producing mutants thereof.

As the microorganisms belonging to the genus Corynebacterium or Brevibacterium, any of the microorganisms which are known as glutamic acid-producing coryneform bacteria may be used. The following are preferred.

| | |
|---|---|
| Corynebacterium glutamicum | ATCC 13032 |
| Corynebacterium acetoacidophilum | ATCC 13870 |
| Corynebacterium herculis | ATCC 13868 |
| Corynebacterium lilium | ATCC 15990 |
| Corynebacterium melassecola | ATCC 17965 |
| Brevibacterium divaricatum | ATCC 14020 |
| Brevibacterium flavum | ATCC 14067 |
| Brevibacterium immariophilium | ATCC 14068 |
| Brevibacterium lactofermentum | ATCC 13869 |
| Brevibacterium thiogenitalis | ATCC 19240 |

Aromatic amino acid-producing mutants derived from the above strains are more preferable. These mutants can be obtained as strains having, amino acid-requirement and/or resistance to amino acid analogues [Journal of Japan Agricultural Chemistry Association, 50, (1) p. R. 79 (1976)].

As the vector for inserting said DNAs, any plasmid that is autonomously replicable in microorganisms belonging to the genus Corynebacterium or Brevibacterium may be used. For example, such plasmids as pCG1 [Japanese Published Unexamined Patent Application No. 134500/1982 (EP 58889-B and U.S. Pat. No. 4,617,267)], pCG2 [Japanese Published Unexamined Patent Application No. 35197/1983 (EP 73062-B and U.S. Pat. No. 4,489,160)], pCG4 and pCG11 [Japanese Published Unexamined Patent Application No. 183799/1982 (EP 63763-B and U.S. Pat. No.

4,500,640)], pCE54 and pCB101 [Japanese Published Unexamined Patent Application No. 105999/1983 (EP 82485-A and U.S. Pat. No. 4,710,471)], and pCE51, pCE52, and pCE53 [Molecular and General Genetics, 196, 175 (1984)] may be used.

A recombinant DNA composed of a vector DNA and a donor DNA containing a gene coding for DS can be obtained as a mixture with various recombinant DNAs by the conventional methods which comprises cleaving the two DNA's with restriction enzymes within a test tube followed by, if necessary, treatment of the cleaved ends with a terminal transferase or DNA polymerase, and ligating both DNAs with DNA ligase [Methods in Enzymology, 68, (1979)]. The mixture of ligated DNAs thus obtained is used to transform a mutant strain of the genus Corynebacterium or Brevibacterium deficient in a gene coding for DS, and a transformant in which such deficiency is removed is selected. The recombinant DNA containing the gene coding for DS can be obtained by isolating the plasmid from the transformant obtained as above. Transformation of a microorganism of the genus Corynebacterium or Brevibacterium can be carried out by the method which uses protoplasts [Japanese Published Unexamined Patent Application Nos. 186492/1982 (EP 63764-A and U.S. Pat. No. 4,683,205) and 186489/1982 (EP 64680-B and U.S. Pat. No. 4,681,847)].

In the same manner as described above, a recombinant DNA composed of a vector DNA and a donor DNA containing genes relating to the biosynthesis of tryptophan can be obtained; that is, by transforming a tryptophan-requiring mutant of the genus Corynebacterium or Brevibacterium which is deficient in tryptophan biosynthesis with a mixture of recombinant DNAs composed of the chromosomal DNA and the vector DNA, and selecting a transformant having no tryptophan requirement, followed by isolation of the recombinant DNA from the transformant. The identification of the genes relating to the tryptophan biosynthesis can be carried out by a complementation test using tryptophan-requiring mutants derived from a microorganism belonging to the genus Corynebacterium, Brevibacterium or Escherichia and having the relevant deficiency.

As demonstrated in Example 1 (3), when the chromosomal DNA of *Corynebacterium glutamicum* is adopted as the donor, all of genetic information concerning the synthesis of AS, PRT, PRAI, InGPS and TS, which are the enzymes relating to the biosynthesis of tryptophan, is isolated as the BamHI DNA fragment of 11.0 kilobase (kb).

A recombinant DNA composed of a vector DNA and a donor DNA containing PGDH gene can be obtained in a similar manner; that is, by transforming a serine-requiring mutant belonging to the genus Corynebacterium or Brevibacterium deficient in PGDH gene with a mixture of recombinant DNAs composed of the chromosomal DNA and the vector DNA, and selecting a transformant which has no serine requirement.

By excising the relevant gene-containing DNA fragments from the recombinant DNA containing the DS gene, the recombinant DNA containing the genes relating to the tryptophan biosynthesis, and the recombinant DNA containing the PGDH gene, and sequentially recombining the cleaved DNA fragments, there is obtained a recombinant DNA which contains all of the genes mentioned above. The genes mentioned above can simultaneously be amplified by introducing the recombinant DNA into a host microorganism. Otherwise, these genes can also be amplified, if they are incorporated into separate vector DNAs capable of coexisting in the same cell and these vector plasmids are simultaneously introduced in a host microorganism.

When the recombinant DNA mentioned above contains a DS gene, genes relating to the tryptophan biosynthesis, and a PGDH gene of the wild-type derived from a microorganism of the genus Corynebacterium or Brevibacterium, the amounts of individual enzymes synthesized is synergistically increased and tryptophan productivity of the host microorganism is increased. However, it has been known that, in microorganisms of the genus Corynebacterium or Brevibacterium, DS is subject to feedback inhibition by phenylalanine and tyrosine, and AS and PRT are subject to feedback inhibition by tryptophan [Agricultural and Biological Chemistry, 39, 351 (1975) and ibidem, 47, 2295 (1983)]. It is, therefore, preferable to use a recombinant DNA containing mutant genes coding for DS, AS and PRT free from such feedback inhibition in order to ensure higher L-tryptophan productivity in a microorganism of the genus Corynebacterium or Brevibacterium. The mutant DS, AS and PRT genes can be obtained by using as a donor the chromosomal DNA of a mutant of the genus Corynebacterium or Brevibacterium whose DS, AS or PRT is free from feedback inhibition. Selection of the mutant genes can be carried out based on complementation of deficiency of the DS gene or the genes relating to tryptophan biosynthesis as described above. The cloning may be otherwise carried out by using, as a recipient, a strain of the genus Corynebacterium or Brevibacterium containing wild-type DS or AS and PRT and by selecting a transformant resistant to a phenylalanine analogue such as, for example, p-fluorophenylalanine (hereinafter referred to as "PFP") or a tryptophan analogue such as, for example, 5-fluorotryptophan (hereinafter referred to as "5FT"). The preparation of the recombinant DNA containing the mutant genes coding for DS, AS and PRT may be carried out by the same method as in the preparation of the recombinant DNA containing the wild-type genes. The recombinant DNA containing the mutant genes coding for DS, AS and PRT can be alternatively prepared by in vitro mutagenesis of the recombinant DNA containing the wild-type genes according to the method described in Molecular and General Genetics, 145, 101 (1978), or by in vivo mutagenesis of a microorganism carrying the recombinant DNA containing the wild-type genes according to the conventional method. The recombinant DNA which simultaneously contains the wild-type or mutant DS gene, the genes relating to the tryptophan biosynthesis, and PGDH gene can be introduced into a microorganism of the genus Corynebacterium or Brevibacterium by the transformation method using protoplasts as mentioned above.

Production of L-tryptophan using such a transformant carrying the recombinant plasmid can be carried out by the same method as in a conventional process for producing an amino acid by fermentation. The transformant is cultured in an ordinary culture medium containing carbon sources, nitrogen sources, inorganic substances, amino acids, vitamins and other nutrients under aerobic conditions at a controlled temperature, pH, etc., and L-tryptophan accumulated in the culture is recovered therefrom.

As the carbon sources, various carbohydrates such as glucose, glycerol, fructose, sucrose, maltose, mannose, starch, starch hydrolyzate and molasses; polyalcohols;

and various organic acids such as pyruvic acid, fumaric acid, lactic acid and acetic acid may be used. Hydrocarbons and alcohols may also be used depending on the assimilability of the strain employed. Particularly, cane molasses is used advantageously.

As the nitrogen sources, ammonia; various inorganic and organic ammonium salts such as ammonium chloride, ammonium sulfate, ammonium carbonate and ammonium acetate; urea and other nitrogen-containing substances; and nitrogen-containing organic substances such as peptone, NZ-amine, meat extract, yeast extracts, corn steep liquor, casein hydrolyzates, fish meal or its digested products, and chrysalis hydrolyzates may be used.

As the inorganic substances, dipotassium hydrogen phosphate, potassium dihydrogen phosphate, ammonium sulfate, ammonium chloride, magnesium sulfate, sodium chloride, ferrous sulfate, manganese sulfate, calcium carbonate, etc. may be used. Amino acids and vitamins such as biotin and thiamine may also be added if necessary, depending on the carbon and nitrogen sources in the medium used. In addition, when the strain used requires a specific substance for the growth, it is necessary to add such substance to the medium.

Cultivation is carried out under aerobic conditions, for example, by shaking the culture or by aeration-stirring of the culture, preferably at a temperature in the range of 20° to 40° C. The pH of the medium is preferably maintained around neutral during the cultivation. L-tryptophan is accumulated in the medium usually by culturing for one to five days. After the completion of cultivation, the cells are removed from the culture by filtration or centrifugation and the filtrate or supernatant thus separated is treated in a known manner (e.g., treatment with activated carbon and ion-exchange resins) to recover L-tryptophan.

L-tryptophan can thus be produced in higher yields by using a strain of the genus Corynebacterium or Brevibacterium carrying a recombinant DNA that contains the DS gene, the genes relating to the biosynthesis of L-tryptophan and PGDH gene.

In this specification, there is shown an Example where the productivity of L-tryptophan is increased by introducing a recombinant DNA containing all of the DS, AS, PRT, PRAI, InGPS, TS and PGDH genes into *Corynebacterium glutamicum*. However, the intended object can also be attained by using any other glutamic acid-producing coryneform bacteria in place of *Corynebacterium glutamicum*.

In spite of many common microbiological properties, so called glutamic acid-producing coryneform bacteria having high glutamic acid productivity are classified to various species by researchers and even to different genera such as Corynebacterium and Brevibacterium probably because of their industrial importance. However, it has been pointed out that these microorganisms should be classified as one species because they have the same amino acid composition of cell walls and the same DNA-base composition. Further, it has been reported that these microorganisms show more than 70–80% homology in DNA-DNA hybridization, indicating that the microorganisms are very closely related [refer to Komatsu, Y.: Report of the Fermentative Research Institute, No. 55, 1 (1980), and Suzuki, K., Kaneko, T., and Komagata, K.: Int. J. Syst. Bacteriol., 31, 131 (1981)]. On considering the above-mentioned very close relationship of glutamic acid-producing microorganisms, it is readily assumed that the present invention is applicable to all of the glutamic acid-producing coryneform bacteria. The applicability of the present invention depends on whether the recombinant DNA is autonomously replicable in the glutamic acid-producing coryneform bacteria and whether the DS gene, the genes relating to the L-tryptophan biosynthesis and PGDH gene are expressed therein and such a small differences in DNA homology among the glutamic acid-producing coryneform bacteria are negligible. It is apparent that the glutamic acid-producing coryneform bacteria have the common function to allow replication of plasmids and expression of genes from the fact that plasmid pCG4 which is isolated from *Corynebacterium glutamicum* 225-250 (Japanese Published Unexamined Patent Application No. 183799/1982) and which has spectinomycin and/or streptomycin resistant gene(s) can be replicated and the gene(s) can be expressed in glutamic acid-producing coryneform bacteria such as strains of the genera Corynebacterium and Brevibacterium (Japanese Published Unexamined Patent Application No. 186492/1982). Therefore, the process for the construction of an L-tryptophan-producing microorganism by introducing a recombinant DNA containing all of the DS, AS, PRT, PRAI, InGPS, TS and PGDH genes is applicable not only to *Corynebacterium glutamicum*, but also to all the glutamic acid-producing coryneform bacteria including the bacteria of the genera Corynebacterium and Brevibacterium.

Figure 1:
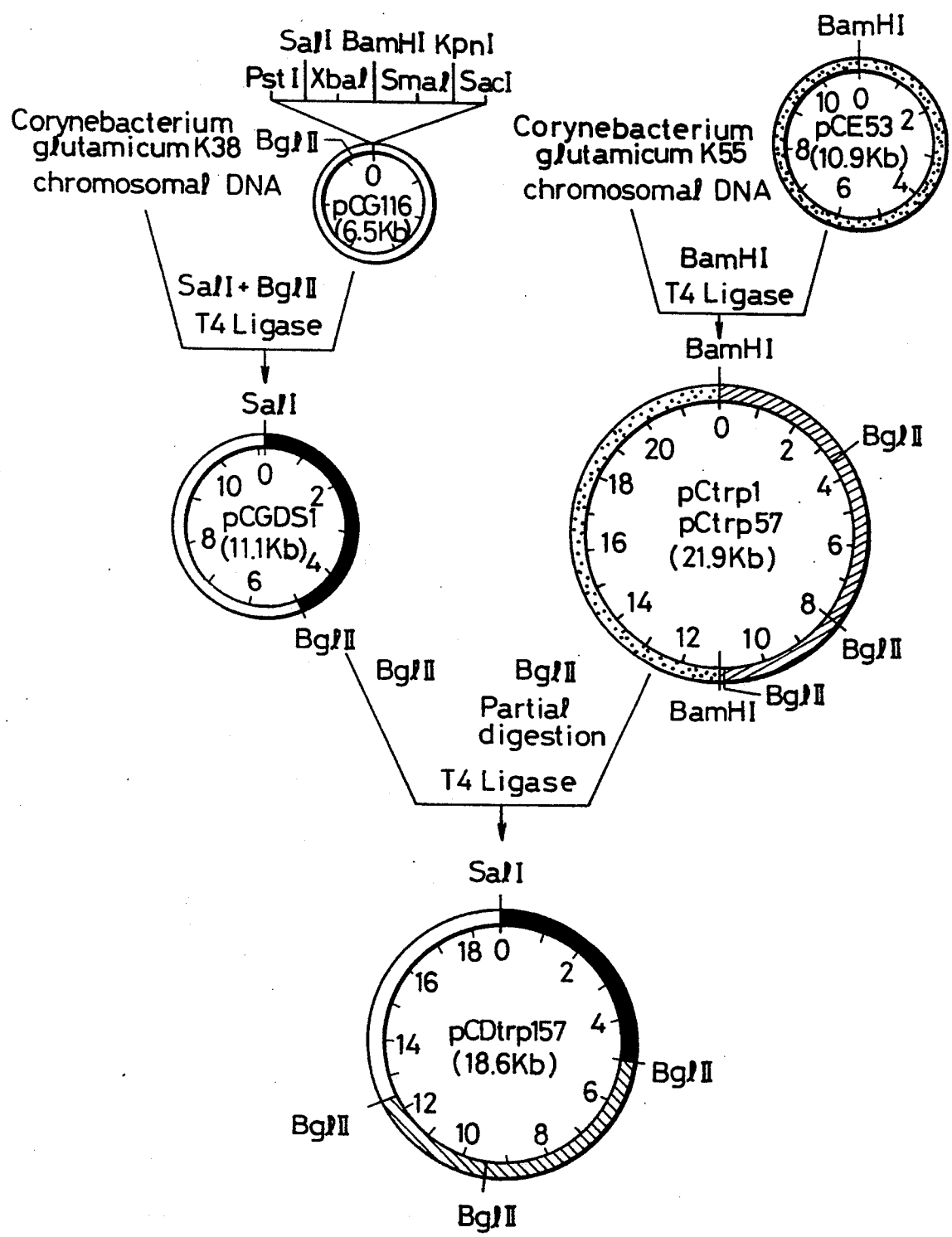
FIG. 1 and FIG. 2 show respectively the cleavage maps of pCDtrp157 and pDTS9901 for restriction enzymes, and the steps for constructing the plasmids. The DS gene is contained in the chromosomal DNA fragment indicated by the thick solid line, the genes relating to the tryptophan biosynthesis are contained in the chromosomal DNA fragment indicated by shading, the PGDH gene is contained in the chromosomal DNA fragment indicated by the broken line. The sizes of plasmid are expressed in kilobase (Kb).

The present invention is further illustrated by the following Example.

EXAMPLE 1

Production of L-tryptophan by a strain carrying a recombinant plasmid that contains DS gene of *Corynebacterium glutamicum* K38, all of the genes relating to the synthesis of AS, PRT, PRAI, InGPS and TS of *Corynebacterium glutamicum* K55 and PGDH gene of *Corynebacterium glutamicum* ATCC 31833

(1) Preparation of chromosomal DNAs of *Corynebacterium glutamicum* K38 (FERM BP-454), *Corynebacterium glutamicum* K55 (FERM BP-864) and *Corynebacterium glutamicum* ATCC 31833 and vector plasmids pCE53 and pCG116: *Corynebacterium glutamicum* K38 (FERM BP-454), which is resistant to PFP and p-aminophenylalanine, *Corynebacterium glutamicum* K55 (FERM BP-864), which is requiring phenylalanine and tyrosine and resistant to 5-methyltryptophan, tryptophan hydroxamate, 6-fluorotryptophan, 4-methyltryptophan, PFP, p-aminophenylalanine, tyrosine hydroxamate and phenylalanine hydroxamate, and *Corynebacterium glutamicum* ATCC 31833 were respectively cultured in NB medium (20 g/l bouillon powder and 5 g/l yeast extract; pH 7.2). The resulting seed cultures (20 ml each) were respectively inoculated into 400 ml of semi-synthetic medium SSM [20 g/l glucose, 10 g/l (NH$_4$)$_2$SO$_4$, 3 g/l urea, 1 g/l yeast extract, 1 g/l KH$_2$PO$_4$, 0.4 g/l MgCl$_2$.6H$_2$O, 10 mg/l FeSO$_4$.7H$_2$O, 0.2 mg/l MnSO$_4$.4–6H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 30 μg/l biotin and 1 mg/l thiamine hydrochloride; pH 7.2] containing 100 μg/ml each of phenylalanine and tyrosine, and were cultured with shaking at 30° C. The optical density (OD) at 660 nm (hereinafter the optical density is measured at 660 nm unless otherwise specified) was determined with a Tokyo Koden colorimeter, and when the OD reached 0.2, penicillin G was added to a concentration of 0.5 unit/ml. Culturing was further continued until OD reached 0.6.

The grown cells were collected from the culture and washed with TES buffer solution [0.03M tris(hydroxymethyl)aminomethane (hereinafter abbreviated to "Tris"), 0.005M disodium ethylenediaminetetraacetate (hereinafter abbreviated to EDTA) and 0.05M NaCl; pH 8.0]. The washed cells were suspended in 10 ml of a lysozyme solution (25% sucrose, 0.1M NaCl, 0.05M Tris and 0.8 mg/ml lysozyme; pH 8.0), and allowed to react at 37° C. for two hours. High molecular chromosomal DNAs were isolated from the collected cells according to the method of Saito, H. and Miura, K. [Biochim. Biophys. Acta, 72, 619 (1963)].

pCE53 used as a vector is constructed by ligating plasmid pCG1 autonomously replicable in *Corynebacterium glutamicum* with plasmid pGA22 autonomously replicable in *Escherichia coli* (refer to G. An, et al.: J. Bacteriol. 140, 400 (1979)]. It is constructed by ligating both DNAs at the BglII-cleavage site of pCG1 and one of the two BamHI-cleavage sites of pGA22, which is out of the tetracycline resistance region, utilizing the same cohesive ends. pCE53 has selection markers such as kanamycin-resistance derived from pGA22 and a single cleavage site for restriction enzyme BamHI.

pCG116, also used as a vector, is constructed by ligating a linker obtained from M13mp18 RF DNA (Takara Shuzo Co., Ltd.) with the StuI-PstI-cleaved DNA fragment of pCG11 autonomously replicable in *Corynebacterium glutamicum* by utilizing their blunt ends and cohesive ends. The linker is obtained by cleaving M13mp18 RF DNA with EcoRI, repairing the cohesive end to blunt end with Klenow fragment (Takara Shuzo Co., Ltd.), and again cleaving the DNA with PstI. Plasmid pCG116 has a molecular size of about 6.5 Kb and a single cleavage site for each of BglII, PstI, SalI, XbaI, BamHI, SmaI, KpnI and SacI, and gives a streptomycin- and/or spectinomycin-resistance phenotype (see FIG. 1).

pCE53 and pCG116 were isolated individually from cultured cells of *Corynebacterium glutamicum* ATCC 13032 or *Corynebacterium glutamicum* 31833, carrying pCE53 or pCG116, according to the procedure described below.

*Corynebacterium glutamicum* ATCC 13032 or *Corynebacterium glutamicum* ATCC 31833, carrying pCE53 or pCG116 was cultured with shaking at 30° C. in 400 ml of SSM medium and treated with penicillin G in the same manner as above, and culturing was further continued until OD reached about 0.6. The grown cells were collected, washed with TES buffer solution, and suspended in 10 ml of a lysozyme solution. The suspension was allowed to react at 37° C. for two hours. To the reaction mixture were successively added 2.4 ml of 5M NaCl, 0.6 ml of 0.5M EDTA (pH 8.5) and 4.4 ml of a solution comprising 4% sodium laurylsulfate and 0.7M NaCl, and the resulting mixture was gently stirred and placed on ice for 15 hours. The lysate thus obtained was transferred to a centrifuge tube and subjected to centrifugation at 69,400×g at 4° C. for 60 minutes to recover a supernatant. Then, polyethylene glycol (PEG) 6,000 (Nakarai Chemicals, Ltd.) was added thereto in an amount corresponding to 10% by weight. The mixture was gently stirred, and then placed on ice. After ten hours, the mixture was centrifuged at 1,500×g for ten minutes to recover pellet. Then, 5 ml of TES buffer solution was added to dissolve the pellet gradually, and 2.0 ml of 1.5 mg/ml ethidium bromide was added to the solution. Cesium chloride was added to adjust the density of the solution to 1.580.

The solution thus obtained was subjected to ultracentrifugation at 105,000×g at 18° C. for 48 hours, and a high density band at the lower part of the centrifuge tube which was detected under UV irradiation was withdrawn by puncturing the side of the centrifuge tube, using a syringe, to recover the fraction containing pCE53 or pCG116 plasmid DNA. The fraction was extracted five times with an equal volume of isopropanol solution [90% (V/V) isopropanol in TES buffer solution] a saturated with cesium chloride to remove ethidium bromide. Then, the solution was dialyzed against TES buffer solution.

(2) Cloning of a DNA fragment containing DS gene:

To 60 μl of reaction solution Y-100 (10 mM Tris, 6 mM MgCl$_2$ and 100 mM NaCl; pH 7.5) containing 3 μg of pCG116 plasmid DNA isolated from *Corynebacterium glutamicum* ATCC 13032 carrying pCG116 were added 6 units each of restriction enzymes SalI and BglII (Takara Shuzo Co., Ltd.; unless otherwise specified, restriction enzymes hereinafter used are products of Takara Shuzo Co., Ltd.), and the mixture was allowed to react at 37° C. for 60 minutes. The reaction was stopped by adding phenol. Separately, 6 units each of restriction enzymes SalI and BglII were added to 140 μl of reaction solution Y-100 containing 3 μg of the chromosomal DNA of *Corynebacterium glutamicum* K38 (FERM BP-454) obtained as above, and the mixture was allowed to react at 37° C. for 60 minutes. The reaction was stopped by treatment with phenol. Both reaction mixtures thus obtained were mixed, and twice the volume of ethanol was added to precipitate DNA. The DNA was recovered and suspended in 200 μl of water.

To the DNA suspension thus obtained were added 40 μl of a buffer solution for T4 ligase at a 10-fold concentration (660 mM Tris, 66 mM MgCl$_2$ and 100 mM dithiothreitol; pH 7.6), 40 μl of 5 mM ATP, 300 units of T4 ligase (Takara Shuzo Co., Ltd.) and 120 μl of water, and the mixture was allowed to react at 12° C. for 16 hours.

The reaction mixture was used for transformation of *Corynebacterium glutamicum* ATCC 13032. A seed culture of this strain (4 ml) was inoculated into 40 ml of SSM medium, and cultured with shaking at 30° C. When OD reached 0.2, the culture was treated with penicillin G in the same manner as in (1) above, and culturing was further continued until OD reached 0.6. The grown cells were collected and suspended to a concentration of about 10$^9$ cells per milliliter in 10 ml of RCGP medium [5 g/l glucose, 5 g/l casamino acid, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$.7H$_2$O, 2 mg/l MnSO$_4$.4–6H$_2$O, 0.9 mg/l ZnSO$_4$.7H$_2$O, 0.04 mg/l (NH$_4$)$_6$Mo$_7$O$_{24}$.4H$_2$O, 30 μg/l biotin, 2 mg/l thiamine hydrochloride, 135 g/l disodium succinate and 30 g/l polyvinyl pyrrolidone (M.W.: 10,000); pH 7.6] containing 1 mg/ml lysozyme. The suspension was transferred to an L-type test tube and gently shaken at 30° C. for 16 hours to prepare protoplasts.

Then, 0.5 ml of the protoplast suspension was taken in a small test tube and centrifuged at 2,500×g for five minutes to separate the protoplasts. The protoplasts were suspended in 1 ml of TSMC buffer solution (10 mM MgCl$_2$, 30 mM CaCl$_2$, 50 mM Tris and 400 mM sucrose; pH 7.5) and washed by centrifugation. The washed protoplasts were resuspended in 0.1 ml of TSMC buffer solution. Then, 100 μl of a 1:1 mixture of TSMC buffer solution at a two-fold concentration and the ligase reaction mixture obtained above was added to the protoplast suspension, and the resulting mixture was admixed with 0.8 ml of TSMC buffer solution containing 20% PEG 6000. After three minutes, 2 ml of RCGP medium (pH 7.2) was added thereto and the resulting mixture was centrifuged at 2,500×g for five minutes to remove a supernatant. The precipitated protoplasts were suspended in 1 ml of RCGP medium, and the suspension (0.2 ml) was spread on RCGP agar medium (RCGP medium containing 1.4% agar; pH 7.2) containing 400 μg/ml spectinomycin and cultured at 30° C. for seven days.

The colonies grown on RCGP agar medium were scraped up, and washed twice with physiological saline solution by centrifugation. The washed cells were suspended in 1 ml of physiological saline solution. The suspension was spread on minimal agar medium M1 [10 g/l glucose, 1 g/l (NH$_4$)H$_2$PO$_4$, 0.2 g/l KCl, 0.2 g/l MgSO$_4$.7H$_2$O, 10 mg/l FeSO$_4$.7H$_2$O, 0.2 mg/l MnSO$_4$.4-6H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 50 g/l biotin, 2.5 mg/l p-aminobenzoic acid, 1 mg/l thiamine hydrochloride and 16 g/l agar; pH 7.2] containing 3 mg/ml PFP and 100 μg/ml spectinomycin. Culturing was carried out at 30° C. for five days, and transformants which are resistant to PFP and spectinomycin were selected.

Plasmid DNAs were isolated from the selected transformants in the same manner as in the isolation of pCG116 in (1) above. Digestion with various restriction enzymes and analysis by agarose gel electrophoresis revealed that the plasmid DNA isolated from one of the transformants and named pCGDS1 has a structure in which a SalI-BglII-cleaved DNA fragment of 5.0 Kb has been inserted into the SalI-BglII-cleavage site of pCG116 (see FIG. 1).

DS activities of *Corynebacterium glutamicum* ATCC 13032 and the transformant carrying pCGDS1 were determined according to the method of P. R. Sprinavasan, D. B. Sprinson, et al. [J. Biol. Chem., 234, 716 (1959)]. It was demonstrated that DS activity of the transformant carrying pCGDS1 is 8 to 10 times as high as that of the parent strain and DS in the transformant is free from inhibition by phenylalanine and tyrosine. This indicates that the DNA fragment of 5.0 Kb introduced in pCGDS1 contains DS gene derived from *Corynebacterium glutamicum* K38.

(3) Cloning of a DNA fragment carrying all of genetic information relating to the synthesis of AS, PRT, PRAI, InGPS and TS:

To 60 μl of reaction solution Y-100 containing 3 μg of pCE53 plasmid DNA isolated from *Corynebacterium glutamicum* ATCC 13032 carrying pCE53 was added 6 units of restriction enzyme BamHI, and the mixture was allowed to react at 37° C. for 60 minutes. The reaction was stopped by heating at 65° C. for 10 minutes. Separately, 6 units of restriction enzyme BamHI was added to 140 μl of reaction solution Y-100 containing 3 μg of the chromosomal DNA of *Corynebacterium glutamicum* K55 (FERM BP-864) obtained in (1) above, and the mixture was allowed to react at 37° C. for 60 minutes. The reaction was stopped by heating at 65° C. for 10 minutes.

Both reaction mixtures thus obtained were mixed, and 40 μl of buffer solution for T4 ligase at a 10-fold concentration, 40 μl of 5 mM ATP, 300 units of T4 ligase and 120 μl of water were added to the mixture. The resulting mixture was allowed to react at 12° C. for 16 hours.

The reaction mixture was used for transformation of *Corynebacterium glutamicum* TA108, a strain requiring for tryptophan and lacking the gene for β-subunit of TS which has α- and β-subunits [deposited with the Fermentation Research Institute (FRI), Agency of Industrial Science and Technology, Japan under the Budapest Treaty on Apr. 9, 1988 as FERM BP-1846].

A seed culture of TA108 strain (4 ml) was inoculated into 40 ml of SSM medium containing 50 μg/ml tryptophan, and cultured with shaking at 30° C. When OD reached 0.2, treatment with penicillin G was carried out in the same manner as in (1) above, and culturing was continued further until OD reached 0.6. The grown cells were collected and treated with lysozyme in the same manner as in (2), and the protoplasts thus obtained were subjected to transformation in the same manner as in (2) using the ligase reaction mixture prepared as above. The kanamycin-resistant colonies grown on RCGP agar medium containing 200 μg/ml kanamycin were scraped up, and washed twice with physiological saline solution by centrifugation. The washed cells were suspended in 1 ml of physiological saline solution. The suspension was spread on minimal agar medium M1 containing 10 μg/ml kanamycin and cultured at 30° C. for three days, and transformants resistant to kanamycin and not requiring tryptophan were selected. From these transformants were isolated plasmid DNAs in the same manner as in the isolation of pCE53 in (1) above. Digestion with various restriction enzymes and analysis by agarose gel electrophoresis revealed that the plasmid DNA isolated from one of the transformants and named pCtrp1 has a structure in which BamHI-cleaved DNA fragment of 11.0 Kb has been inserted into the BamHI cleavage site of pCE53 (see FIG. 1).

The other L-tryptophan biosynthetic genes which are contained in the BamHI-cleaved 11.0 Kb DNA fragment were identified in the following manner. pCtrp1 was used to transform *Corynebacterium glutamicum* TA105 (a strain lacking the AS gene), TA106 (a strain lacking the PRT gene) and TA107 (a strain lacking the TS-α-subunit gene) in the same manner as described above. It was demonstrated that all of the kanamycin-resistant colonies grown on RCGP agar medium containing 200 μg/ml kanamycin did not require tryptophan for growth. This indicates the presence of the AS, PRT, TS-α and TS-β genes in the above 11.0 Kb DNA fragment introduced into pCtrp1.

Separately, pCtrp1 was used to transform *Escherichia coli* ATCC 23719 (K-12, trpC−) according to the method of M. Dagert, et al. [Gene, 6, 23 (1979)]. It was found that all of the kanamycin-resistant colonies grown on LB agar medium (10 g/l Bacto-Tryptone, 5 g/l yeast extract, 1 g/l glucose, 5 g/l NaCl and 16 g/l agar; pH 7.2) containing 20 μg/ml kanamycin have no requirement for tryptophan. This indicates the presence of the PRAI and InGPS genes in the above 11.0 Kb DNA fragment inserted into pCtrp1.

(4) Preparation of plasmid pCtrp57 resistant to tryptophan analogues:

TA108 strain carrying pCtrp1 was cultured in NB medium containing 10 μg/ml kanamycin till the latter stage of the logarithmic growth phase. The grown cells were collected and washed once with 50 mM Tris-maleate buffer solution (pH 6.0) by centrifugation. The washed cells were treated with 400 μg/ml N-methyl-N'-nitro-N-nitrosoguanidine in 50 mM Tris-maleate buffer solution at room temperature for 20 minutes. The treated cells were washed twice with 50 mM Tris-maleate buffer solution by centrifugation and cultured in NB medium containing 10 μg/ml kanamycin at 30° C. for 16 hours. A plasmid DNA was isolated from the grown cells in the same manner as in (1). TA108 strain was transformed with the plasmid thus obtained in the same manner as in (3), and the kanamycin-resistant Colonies grown on RCGP agar medium containing 200 μg/ml kanamycin were scraped up, and washed twice with physiological saline solution by centrifugation. The washed cells were spread on minimal agar medium M1 containing 3 mg/ml 5FT, and cultured at 30° C. for three days. From the grown colonies were selected those which are capable of growing on M1 agar medium containing 3 mg/ml 5FT and on NB agar medium containing 10 μg/ml kanamycin. A plasmid isolated from one of the selected strains was named pCtrp57.

AS activities of *Corynebacterium glutamicum* ATCC 13032 and TA108 strains carrying pCtrp1 or pCtrp57 were determined according to the method of H. Hagino, et al. [Agric. Biol. Chem., 39, 323 (1975)], and their PRT activities were determined according to the method of J. Ito and C. Yanofsky [J. Biol. Chem., 97, 734 (1969)]. AS and PRT activities of TA108 strains carrying pCtrp1 or pCtrp57 were more than 10 times as high as those of ATCC 13032 strain. Tryptophan concentrations effective for 50% inhibition of the AS activities of ATCC 39019 strain, TA108 strain carrying pCtrp1 and TA108 strain carrying pCtrp57 were 0.002 mM, 0.008 mM and 4.0 mM, respectively, while tryptophan concentrations effective for 50% inhibition of the PRT activities of these three strains were 0.19 mM, 0.19 mM and 4.8 mM, respectively. This indicates that AS and PRT encoded by pCtrp57 are less sensitive to tryptophan by a factor of about 500 and about 25, respectively, compared with AS and PRT encoded by pCtrp1.

(5) Sub-cloning of a DNA fragment containing all of genetic information relating to the synthesis of AS, PRT, PRAI, InGPS and TS in pCGDS1:

To 100 μl of reaction solution Y-100 containing 5 μg of pCtrp57 plasmid DNA was added 0.5 unit of BglII, and the mixture was allowed to react at 37° C. for ten minutes to effect partial digestion. The DNA fragment of 7.5 Kb thus formed was isolated from agarose gel [Molecular Cloning, 164 (1982)]. Separately, 5 units of BglII was added to 100 μl of reaction solution Y-100 containing 3 μg of pCGDS1 plasmid DNA, and the mixture was allowed to react at 37° C. for 60 minutes. The reaction was stopped by treatment with phenol. Both reaction mixtures thus obtained were mixed, and twice the volume of ethanol was added to precipitate DNA. The DNA was recovered and suspended in 200 μl of water.

To 200 μl of the DNA suspension were added 40 μl of buffer solution for T4 ligase at a 10-fold concentration, 40 μl of 5 mM ATP, 300 units of T4 ligase and 120 μl of water, and the mixture was allowed to react at 12° C. for 16 hours.

The reaction mixture thus obtained was used for transformation of TA108 strain in the same manner as in (3).

The spectinomycin-resistant colonies grown on RCGP agar medium containing 400 μg/ml spectinomycin were scraped up, and washed twice with physiological saline solution by centrifugation. The washed cells were suspended in 1 ml of physiological saline solution. The cell suspension was spread on minimal agar medium M1 containing 3 mg/ml PFP and 100 μg/ml spectinomycin, and cultured at 30° C. for three days. From the grown colonies were selected transformants resistant to PFP and spectinomycin and not requiring tryptophan. Plasmid DNAs were isolated from these transformants in the same manner as in (1). Digestion with various restriction enzymes and analysis by agarose gel electrophoresis revealed that the plasmid DNA isolated from one of the transformants and named pCDtrp157 has a structure in which two BglII-cleaved DNA fragments of 4.5 Kb and 3.0 Kb have been inserted into the BglII cleavage site of pCGDS1 (see FIG. 1).

In order to confirm the presence of all of genetic information relating to the synthesis of AS, PRT, PRAI, InGPS and TS, plasmid pCDtrp157 was subjected to the partial digestion with BglII in the same manner as above, and a DNA fragment of 7.5 Kb was isolated from agarose gel, which was then ligated with pCE53 previously cleaved with BamHI. The product was used for transformation of TA108 strain in the same manner as above, and transformants resistant to kanamycin and not requiring tryptophan were selected. Digestion with various restriction enzymes and analysis by agarose gel electrophoresis revealed that the plasmid DNA isolated from one of the transformants and named pCtrp577 has a structure in which two BglII-cleaved DNA fragments of 4.5 Kb and 3.0 Kb have been inserted into the BamHI cleavage site of pCE53. Identification of the genes relating to the tryptophan biosynthesis was carried out in the same manner as in (3) using pCtrp577, whereby it was confirmed that all of genetic information relating to the synthesis of AS, PRT, PRAI, InGPS and TS is located on the 7.5 Kb DNA fragment inserted into the BamHI cleavage site of pCE53.

(6) Cloning of a DNA fragment containing PGDH gene:

To 60 μl of reaction solution Y-100 containing 3 μg of pCG116 plasmid DNA isolated from *Corynebacterium glutamicum* ATCC 31833 carrying pCG116 was added 6 units of restriction enzyme SalI, and the mixture was allowed to react at 37° C. for 60 minutes. The reaction was stopped by heating at 65° C. for 10 minutes. Separately, 6 units of restriction enzyme SalI was added to 140 μl of reaction solution Y-100 containing 3 μg of the chromosomal DNA of *Corynebacterium glutamicum* ATCC 31833, and the mixture was allowed to react at 37° C. for 60 minutes. The reaction was stopped by heating at 65° C. for 10 minutes. Both reaction mixtures thus obtained were mixed, and 40 μl of buffer solution for T4 ligase at a 10-fold concentration, 40 μl of 5 mM ATP, 300 units of T4 ligase and 120 μl of water were added to the mixture. The resulting mixture was allowed to react at 12° C. for 16 hours.

Figure 2:
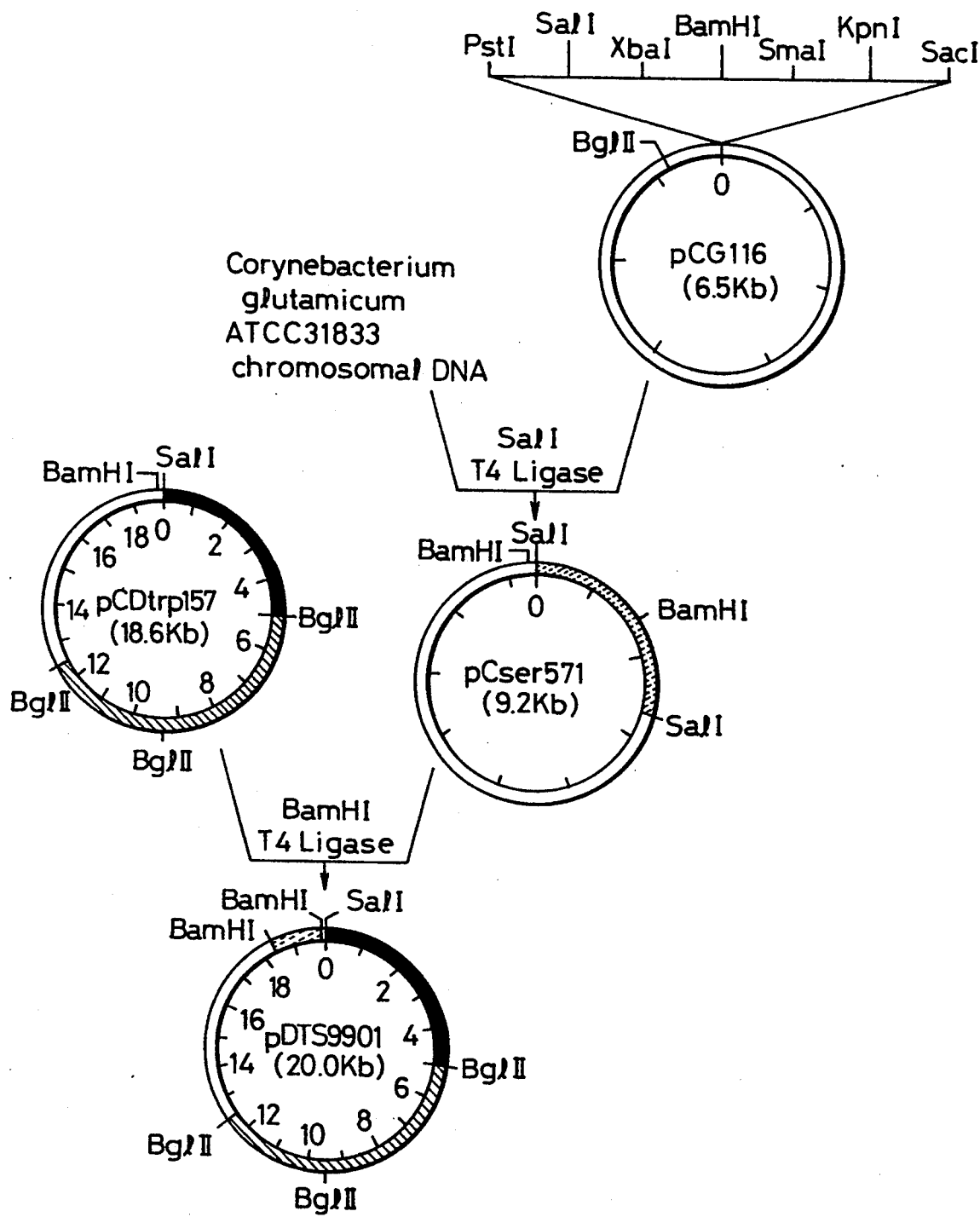

The reaction mixture was used for transformation of *Corynebacterium glutamicum* RS57, a serine-requiring strain lacking the PGDH gene and which is derived from *Corynebacterium glutamicum* ATCC 31833. A seed culture of this strain (4 ml) was inoculated into 40 ml of SSM medium containing 100 μg/ml serine, and cultured with shaking at 30° C. When OD reached 0.2, treatment with penicillin G was carried out in the same manner as in (1) above, and culturing was further continued until OD reached 0.6. The grown cells were collected and treated with lysozyme in the same manner as in (2), and the protoplasts thus obtained were subjected to transformation in the same manner as in (2) using the ligase reaction mixture prepared above. The spectinomycin-resistant colonies grown on RCGP agar medium containing 400 μg/ml spectinomycin were scraped up, and washed twice with physiological saline solution by centrifugation. The washed cells were suspended in 1 ml of physiological saline solution. The suspension was spread on minimal agar medium M1 containing 100 μg/ml spectinomycin and cultured at 30° C. for three days, and transformants resistant to spectinomycin and not requiring serine were selected. From these transformants were isolated plasmid DNAs in the same manner as in the isolation of pCE53 in (1) above. Digestion with various restriction enzymes and analysis by agarose gel electrophoresis revealed that the plasmid DNA isolated from one of the transformants and named pCser571 has a structure in which SalI-cleaved DNA fragment of 2.7 Kb has been inserted into the SalI cleavage site of pCG116 (see FIG. 2).

PGDH activities of *Corynebacterium glutamicum* ATCC 31833 and the transformant carrying pCser571 were determined according to the method of E. Sugimoto and L. I. Pizer [J. Biol. Chem., 243, 2081 (1968)]. It was demonstrated that PGDH activity of the transformant carrying pCser571 is about 13 times as high as that of ATCC 31833 strain. This indicates that the DNA fragment of 2.7 Kb introduced in pCser571 contains PGDH gene.

(7) Ligation of a DNA fragment containing PGDH gene to pCDtrp157:

To 100 μl of reaction solution Y-100 containing 3 μg of pCser571 plasmid DNA was added 6 units of BamHI, and the mixture was allowed to react at 37° C. for 60 minutes. The DNA fragment of 1.4 Kb thus formed was isolated from agarose gel. Separately, 6 units of BamHI was added to 100 μl of reaction solution Y-100 containing 3 μg of pCDtrp157 plasmid DNA, and the mixture was allowed to react at 37° C. for 60 minutes. The reaction was stopped by heating at 65° C. for 10 minutes. Both reaction mixtures thus obtained were mixed, and twice the volume of ethanol was added to precipitate DNA. The DNA was recovered and suspended in 200 μl of water.

To 200 μl of the DNA suspension were added 40 μl of buffer solution for T4 ligase at a 10-fold concentration, 40 μl of 5 mM ATP, 300 units of T4 ligase and 120 μl of water, and the mixture was allowed to react at 12° C. for 16 hours.

The reaction mixture was used for transformation of RS57 strain in the same manner as in (6).

The spectinomycin-resistant colonies grown on RCGP agar medium containing 400 μg/ml spectinomycin were scraped up, and washed twice with physiological saline solution by centrifugation. The washed cells were suspended in 1 ml of physiological saline solution. The cell suspension was spread on minimal agar medium M1 containing 100 μg/ml spectinomycin, and cultured at 30° C. for three days. From the grown colonies were selected transformants resistant to spectinomycin and not requiring serine. Plasmid DNAs were isolated from these transformants in the same manner as in (1). Digestion with various restriction enzymes and analysis by agarose gel electrophoresis revealed that the plasmid DNA isolated from one of the transformants and named pDTS9901 has a structure in which BamHI-cleaved DNA fragment of 1.4 Kb has been inserted into the BamHI cleavage site of pCDtrp157 (refer to FIG. 2).

The plasmid pDTS9901 obtained as above was used for transformation of *Corynebacterium glutamicum* ATCC 21854, a phenylalanine- and tyrosine-requiring strain which is derived from ATCC 13032 strain, in the same manner as in (2), and transformants resistant to spectinomycin were selected.

*Corynebacterium glutamicum* ATCC 21854 carrying pDTS9901 was deposited in the Fermentation Research Institute (FRI), Agency of Industrial Science and Technology, Japan under the Budapest Treaty on Jun. 2, 1989 as *Corynebacterium glutamicum* K82 (FERM BP-2444).

(8) Production of L-tryptophan by strains carrying pCDtrp157 or pDTS9901:

Seed culture (4 ml) of *Corynebacterium glutamicum* BPS-13 (FERM BP-1777), which is a L-tryptophan-producing mutant sensitive to 3-bromopyruvic acid and derived from ATCC 21851 strain, was inoculated into 40 ml of SSM medium containing 50 μg/ml each of phenylalanine and tyrosine, and cultured with shaking at 30° C. When OD reached 0.2, treatment with penicillin G was carried out in the same manner as in (1), and culturing was further continued until OD reached 0.6. The grown cells were collected and treated with lysozyme in the same manner as in (2), and the resulting protoplasts were transformed in the same manner as in (2) using pCDtrp157 or pDTS9901. Plasmid DNAs were isolated from the spectinomycin-resistant transformants thus obtained in the same manner as in (1), and their structures were analyzed by digestion with various restriction enzymes. It was confirmed that these transformants carry pCDtrp157 or pDTS9901.

L-tryptophan production test by test-tube culture was carried out with the above transformants and their parent strain as described below.

Each strain was cultured with shaking in 3 ml of S1 medium (20 g/l glucose, 15 g/l polypeptone, 15 g/l yeast extract, 2.5 g/l NaCl, 1 g/l urea, 200 mg/l L-tyrosine and 200 mg/l L-phenylalanine; pH 7.2) and then inoculated into 5 ml of a production medium P1 [60 g/l glucose, 1 g/l $KH_2PO_4$, 1 g/l $K_2HPO_4$, 1 g/l $MgSO_4.7H_2O$, 20 g/l $(NH_4)_2SO_4$, 10 g/l corn steep liquor, 10 mg/l $MnSO_4$, 30 μg/l biotin and 20 $CaCO_3$; pH 7.2] in a large test tube. Shaking culture was carried out at 30° C. for 72 hours. For the culture of the transformants, 10 μg/l streptomycin was added to the medium. After the culturing was finished, the culture filtrate was subjected to high performance liquid chromatography (HPLC) by the o-phthalaldehyde/2-mercaptoethanol-postcolumn derivatization method to determine the amount of L-tryptophan formed. The results are shown in Table 1.

TABLE 1

| Strain | L-tryptophan (g/l) |
| --- | --- |
| BPS-13 | 7.5 |
| BPS-13/pCDtrp157 | 11.0 |
| BPS-13/pDTS9901 | 11.7 |

(9) Culture test using a 2-liter jar fermentor:

A culture test using a 2-liter jar fermentor was carried out with BPS-13, BPS-13/pCDtrp157 and BPS-13/pDTS9901 strains in the following manner.

Each strain was cultured with shaking in 10 ml of S1 medium at 30° C. for 24 hours. Then, 10 ml of the first seed culture obtained was inoculated into 120 ml of S2 medium [50 g/l sucrose, 2 g/l $KH_2PO_4$, 0.5 g/l $MgSO_4.7H_2O$, 5 g/l $(NH_4)_2SO_4$, 1 g/l urea, 10 mg/l $FeSO_4.7H_2O$, 10 mg/l $MnSO_4.4-6H_2O$, 4 mg/l $CuSO_4.5H_2O$, 40 g/l corn steep liquor, 222 mg/l L-tyrosine, 362 mg/l L-phenylalanine, 50 μg/l biotin, 100 μg/l thiamine hydrochloride and 20 g/l $CaCO_3$; pH 7.2] in a 1-liter Erlenmeyer flask. Shaking culture was carried out at 30° C. for 24 hours. Then, 120 ml of the second seed culture obtained was inoculated into 550 ml of a production medium J1 [63 g/l sucrose, 2 g/l $KH_2PO_4$, 1.2 g/l $K_2HPO_4$, 1.7 g/l $MgSO_4.7H_2O$, 17 g/l $(NH_4)_2SO_4$, 13 mg/l $FeSO_4.7H_2O$, 13 mg/l $MnSO_4.4-6H_2O$, 6 mg/l $CuSO_4.5H_2O$, 66 g/l corn steep liquor, 310 mg/l L-tyrosine, 650 mg/l L-phenylalanine, 230 μg/l biotin and 450 μg/l thiamine hydrochloride; pH 6.8] in a 2-liter jar fermentor. Culturing was carried out at 30° C. with aeration (1 vvm) and agitation (800 rpm) while maintaining the pH at 6.1 by addition of aqueous ammonia. A feed medium (205 ml) [374 g/l sucrose, 0.7 g/l $KH_2PO_4$, 0.5 g/l $K_2HPO_4$ and 600 mg/l L-tyrosine] was added twice during the course of culturing, which was continued until the sugar was completely consumed. For the culture of BPS-13/pCDtrp157 and BPS-13/pDTS9901 strains, 10 μg/ml streptomycin was added to S1, S2 and J1 media. After the culturing was finished, the culture was diluted 1:100 with water and heated at 60° C. for five minutes, and the culture filtrate was subjected to HPLC by the o-phthalaldehyde/2-mercaptoethanol-postcolumn derivatization method to determine the amount of L-tryptophan formed. The results are shown in Table 2.

TABLE 2

| Strain | L-tryptophan (g/l) |
|---|---|
| BPS-13 | 20.1 |
| BPS-13/pCDtrp157 | 32.6 |
| BPS-13/pDTS9901 | 35.2 |

What is claimed is:

1. A recombinant DNA pDTS9901 harbored by *Corynebacterium glutamicum* K89 (FERM BP-2444).

2. A coryneform glutamic acid-producing bacterium belonging to the genus Corynebacterium or Brevibacterium and carrying a recombinant DNA pDTS9901.

* * * * *

UNITED STATES PATENT AND TRADEMARK OFFICE
CERTIFICATE OF CORRECTION

PATENT NO. : 5,407,824                                    Page 1 of 2
DATED      : April 18, 1995
INVENTOR(S): RYOICHI KATSUMATA, et al.

It is certified that error appears in the above-identified patent and that said Letters Patent is hereby corrected as shown below:

ON THE TITLE PAGE:

[56] References Cited

U.S. Patent Documents, "Andeson et al." should read --Anderson et al.--.

Other Publications, "Helmann et al." should read --Herrmann et al.--

COLUMN 1

Line 44, "[journal" should read --[Journal--.

COLUMN 2

Line 54, "having," should read --having--.

COLUMN 6

Line 7, "therein" should read --therein,--; and "a" should be deleted.

COLUMN 8

Line 23, "a" should be deleted; and

Line 58, "OD" should read --OD--.

COLUMN 11

Line 19, "Colonies" should read --colonies--.

UNITED STATES PATENT AND TRADEMARK OFFICE
CERTIFICATE OF CORRECTION

PATENT NO. : 5,407,824
DATED : April 18, 1995
INVENTOR(S) : Ryoichi KATSUMATA, et al It is certified that error appears in the above-identified patent and that said Letters Patent is hereby corrected as shown below:

<u>COLUMN 14</u>

Line 52, "20 $CaCO_3$;" should read --20 g/l $CaCO_3$;--.

Signed and Sealed this

Nineteenth Day of September, 2000

Attest:

Q. TODD DICKINSON

*Attesting Officer*  *Director of Patents and Trademarks*